(12) United States Patent
Solf et al.

(10) Patent No.: US 8,467,848 B2
(45) Date of Patent: Jun. 18, 2013

(54) BIG BORE PET/MR SYSTEM

(75) Inventors: Torsten Solf, Aachen (DE); Volkmar Schulz, Wuerselen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 208 days.

(21) Appl. No.: 13/147,205

(22) PCT Filed: Jan. 12, 2010

(86) PCT No.: PCT/IB2010/050108
§ 371 (c)(1),
(2), (4) Date: Aug. 1, 2011

(87) PCT Pub. No.: WO2010/095063
PCT Pub. Date: Aug. 26, 2010

(65) Prior Publication Data
US 2011/0288401 A1    Nov. 24, 2011

Related U.S. Application Data

(60) Provisional application No. 61/152,984, filed on Feb. 17, 2009.

(51) Int. Cl.
*A61B 5/05* (2006.01)
(52) U.S. Cl.
USPC ........................................................ 600/411
(58) Field of Classification Search
None
See application file for complete search history.

(56) References Cited

U.S. PATENT DOCUMENTS

| | | | | |
|---|---|---|---|---|
| 6,060,883 | A * | 5/2000 | Knuttel | 324/318 |
| 8,131,340 | B2 * | 3/2012 | Eberlein et al. | 600/411 |
| 8,188,736 | B2 * | 5/2012 | Schulz et al. | 324/309 |
| 8,378,677 | B2 * | 2/2013 | Morich et al. | 324/307 |
| 2003/0090267 | A1 | 5/2003 | Rubashov | |
| 2006/0250133 | A1 | 11/2006 | Krieg et al. | |
| 2006/0273795 | A1 | 12/2006 | Rieke et al. | |
| 2008/0284428 | A1 * | 11/2008 | Fiedler et al. | 324/307 |
| 2010/0036237 | A1 * | 2/2010 | Eberlein et al. | 600/411 |
| 2010/0188082 | A1 * | 7/2010 | Morich et al. | 324/307 |
| 2010/0219347 | A1 * | 9/2010 | Schulz et al. | 250/363.04 |

FOREIGN PATENT DOCUMENTS

| WO | 2006071922 A2 | 7/2006 |
|---|---|---|
| WO | WO 2006071922 A2 * | 7/2006 |
| WO | 2008053451 A1 | 5/2008 |
| WO | 2008084438 A2 | 7/2008 |

OTHER PUBLICATIONS

Blindseil, G. A., et al.; Design of a Combined PET and Field-Cycled MRI System for Small Animal Imaging; 2008; Proc. Intl. Soc. Mag. Reson. Med.; 16:351.

Catana, C., et al.; Simultaneous Acquisition of Multislice PET and MR Images: Initial Results with a MR-Compatible PET Scanner; 2006; J. of Nuclear Mediciine; 47(12)1968-1976.

Catana, C., et al.; Simultaneous in vivo positron emission tomography and magnetic resonance imaging; 2008; PNAS; 105(10)3705-3710.

(Continued)

*Primary Examiner* — Long V. Le
*Assistant Examiner* — Bo J Peng

(57) ABSTRACT

A nuclear detector module (24) is housed within an electrically conductive hollow resonator element (18) that is to be used in a combined MR and nuclear imaging unit. The resonator element has an inner face (26) which is radiation transparent facing an examination region (14) and a plurality of other faces (28) disposed facing and spaced from an RF screen (22).

18 Claims, 4 Drawing Sheets

OTHER PUBLICATIONS

Cherry, S. R., et al.; The Integration of Positron Emission Tomography With Magnetic Resonance Imaging; 2008; Proc. of IEEE; 96(3)416-438.

Green, D., et al.; Split cylindrical gradient coil for combined PET-MR system; 2008; Proc. Intl. Soc. Mag. Reson. Med.; 16:352.

Judenhofer, M. S., et al.; PET/MR Images Acquired with a Compact MR-compatible PET Detector in a 7-T Magnet; 2007; Radiology; 244(3)807-814.

Shao, Y., et al.; Simultaneous PET and MR Imaging; 1997; Phys. Med. Biol.; 42:1965-1970.

Shaw, N. R., et al.; Commissioning and Testing of Split Coil MRI System for Combined PET-MR; 2005; Proc. Intl. Soc. Mag. Reson. Med.; 13:407.

Townsend, D. W.; Multimodality imaging of structure and function; 2008; Phys. Med. Biol.; 53(4)R1-R39.

* cited by examiner

BIG BORE PET/MR SYSTEM

CROSS REFERENCE TO RELATED APPLICATIONS

This application claims the benefit of U.S. provisional application Ser. No. 61/152,984 filed Feb. 17, 2009, which is incorporated herein by reference.

The present application relates to the medical imaging arts. It particularly relates to hybrid magnetic resonance (MR) and positron emission tomography (PET) imaging systems, and is described with particular reference thereto. The following relates more generally to diagnostic imaging systems capable of simultaneous or sequential acquisition of SPECT or PET and MR data.

In positron emission tomography (PET), a radiopharmaceutical is administered to the imaging subject, in which the radioactive decay events of the radiopharmaceutical produce positrons. Each positron interacts with an electron to produce a positron-electron annihilation event that emits two oppositely directed gamma rays. Using coincidence detection circuitry, a ring array of radiation detectors surrounding the imaging subject detect the coincident oppositely directed gamma ray events corresponding to the positron-electron annihilation. A line of response (LOR) connecting the two coincident detections contains the position of the positron-electron annihilation event. Such lines of response are analogous to projection data and can be reconstructed to produce a two- or three-dimensional image. In time-of-flight PET (TOF-PET), the small time difference between the detection of the two coincident γ ray events is used to localize the annihilation event along the LOR (line of response). In depth-of-interaction PET (DOI-PET), multi-layered PET detectors are able to determine the depth of γ photon within a scintillation crystal.

In magnetic resonance imaging (MRI), the nuclear spins of the body tissue to be examined are aligned by a static main magnetic field $B_0$ and are excited by transverse magnetic fields $B_1$ oscillating in the radiofrequency (RF) band. The resulting relaxation signals are exposed to gradient magnetic fields to localize the resultant resonance. The relaxation signals are received and reconstructed in a known manner into a single or multiple dimension image.

Hybrid PET/MR imaging systems offer truly simultaneous acquisition and promise to bridge the gap between anatomical imaging and biochemical or metabolic imaging. Early prototypes employed a scintillation crystals coupled to long fiber-optic bundle that ran outside the MR system to isolate the photomultiplier tubes (PMTs) from the magnetic field of the MR system, see Hammer U.S. Pat. No. 4,939,464. The long fibers result in a loss of scintillation light, affecting resolution and crystal identification, thus yielding poor performance. PMTs were later integrated into the static magnet known as split magnet designs. These systems relied on costly magnet designs and allowed for the PET imaging within a small time frame when polarizing and readout fields were switched off.

Solid state photodetectors that are insensitive to magnetic fields offer a number of potential single gantry designs. Silicon photomultipliers (SiPMs) composed of avalanche photodiodes operating in the Geiger mode offer fast performance, high resolution, high gain, excellent signal-to-noise ratio (SNR), and a reduction in necessary circuitry.

One type of PET/MR scanner adjoin standard PET and MRI scanners side-by-side. With the PET circuitry outside of the MR field, the two systems can be readily integrated. The drawback of this configuration is that the PET and MRI data are acquired sequentially and the patient is moved between scanners. Thus, image quality and alignment of imagines is adversely affected. The lengthy acquisition times raise timing issues, particularly with contrast agents. In a combined PET/MR scanner, SiPM based PET detectors are received in a central gap in the gradient coils. In this design, RF shielding is placed between the RF coil of the MRI and the PET detectors to suppress leakage. The added RF shielding along with the RF coil reduces the effective bore radius by approximately 10-12 centimeters.

The present application provides a new and improved PET detector and RF coil arrangement in hybrid PET/MR imaging systems which overcome the above-referenced problems and others.

In accordance with one aspect, a combined MR and nuclear imaging unit is provided for use in a combined MR and nuclear imaging system. Each imaging unit comprised of a hollow resonator element that is configured to house a nuclear detector module and an RF screen adjacent to the resonator element. The resonator element is configured to receive and transmit magnetic resonance signals and to shield the nuclear detector from RF interference.

In accordance with another aspect, a method is provided for making a combined MR and nuclear imaging unit for use in a combined MR and nuclear imaging system which includes disposing a hollow resonator element around a nuclear detector module such that the faces of the resonator element shield the nuclear detector module from RF radiation while allowing γ radiation to pass through one of the faces to the nuclear detector module.

One advantage is an increased bore diameter.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
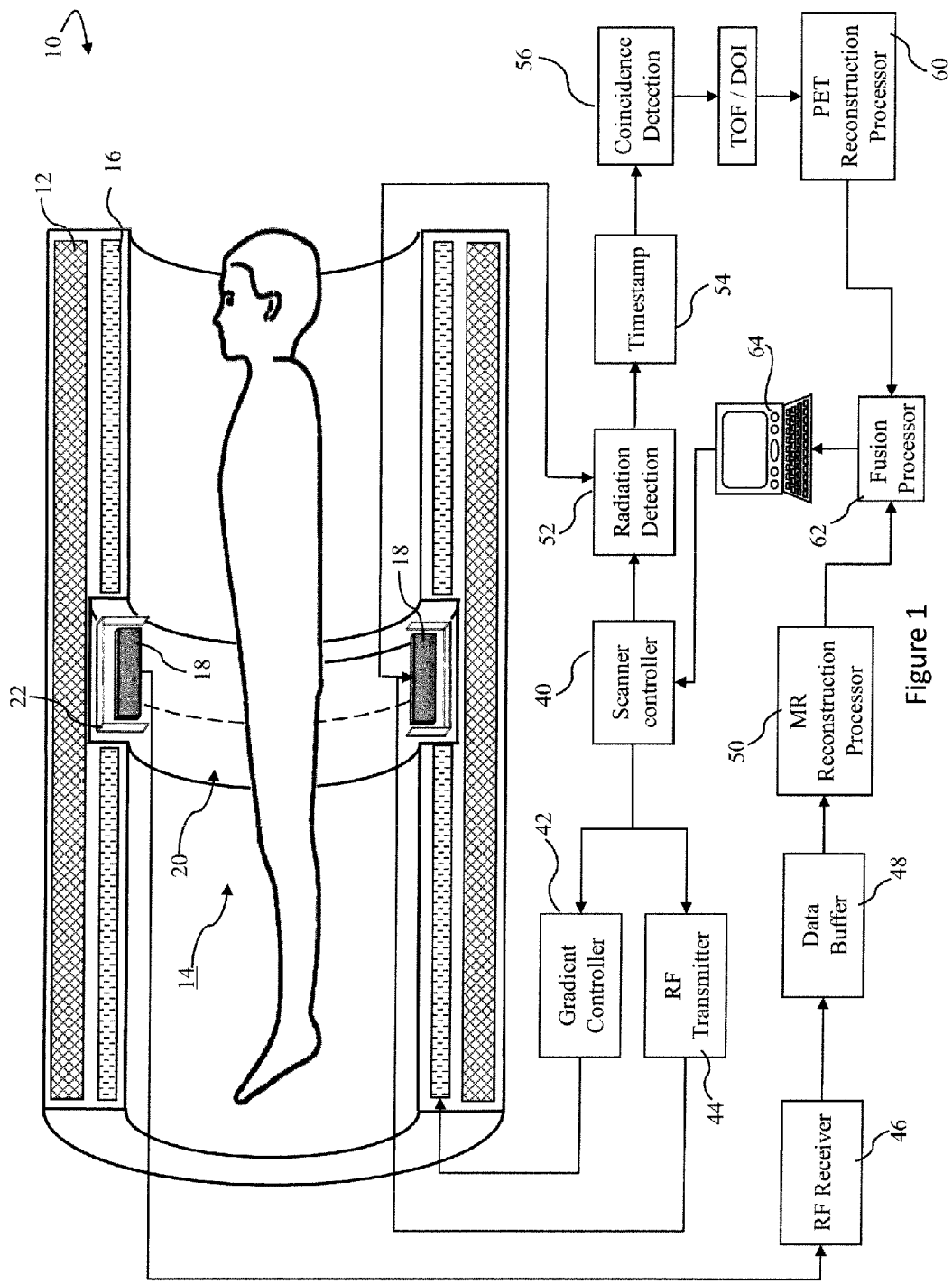
FIG. 1 is a diagrammatic view of a combined PET/MR system.

With reference to FIG. 1, a diagnostic imaging system 10 capable of magnetic resonance imaging and emission radiation imaging, such as PET or SPECT, includes a main magnet 12 which generates a temporally uniform $B_0$ field through an examination region 14. The main magnet may be an annular or bore-type magnet. Gradient magnetic field coils 16 disposed adjacent the main magnet serve to generate magnetic field gradients along selected axes relative to the $B_0$ magnetic field. A radio frequency (RF) coil, such as a ring of transverse electromagnetic (TEM) resonator elements 18 (only two of which are illustrated), is disposed in an annular recess 20 between the gradient coils 16 surrounding the examination region. An RF shield or screen 22 is disposed between the resonator elements and the main magnet and the gradient coils.

The resonator elements 18 are capacitively coupled to the RF screen 22 that surrounds the resonator elements on three sides. A major face of the RF screen 22 is disposed adjacent to the main magnet and parallel to the axial direction of the bore. Two minor faces of the RF screen are generally parallel with the ends of the resonator elements.

Figure 2:
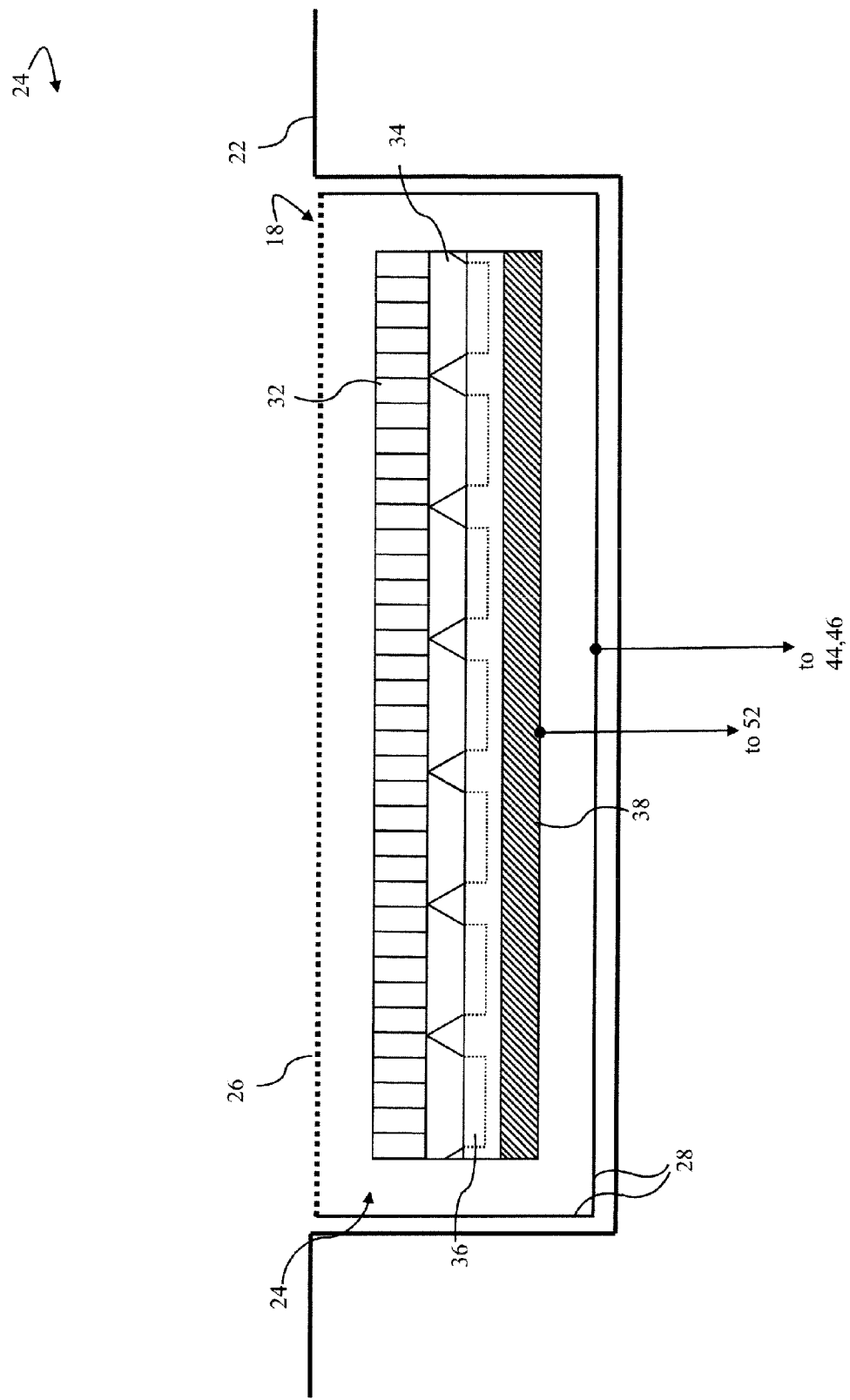
FIG. 2 is a cross-section view of a nuclear detector module housed within a resonator element.

With reference to FIG. 2, the resonator elements 18 each house at least one PET detector module 24. The resonator elements are shaped like a box that not only acts as a conductor capable of transmitting and receiving RF signals, but it is also adapted to shield the PET detector from RF and gradient coil interference. A face 26 of the resonator element adjacent to the examination region 14 is constructed of a radiation transparent material which may include, but not limited to, a conductive screen or mesh, a thin, e.g. 35 μm, copper foil or the like. Other faces 28 of the resonator element box maybe the same conductive material, a laminate of copper foil and a γ ray blocking material such as led, or the like. The PET detector module 24 includes an array of scintillation crystals 32 optically coupled to light guides 34 which propagates photons from the scintillation crystals 32 to an array of sensor tiles 36. Each sensor tile typically includes an array of SiPMs which, in turn, each include an array of Geiger mode APDs. The sensor tiles are electronically connected to application specific integrated circuitry (ASICs) 38 that are responsible for digitizing and pre-processing photon detection events. The circuitry is responsible for radiation detector module identification, pixel identification, timestamps, photon counts, digital biasing circuitry, digital triggering circuitry, and readout circuitry and other functions used in PET imaging with TOF and DOI information. The scintillator crystals 32 are selected to provide high stopping power for the inducement radiation with rapid temporal decay of the scintillation burst. Some suitable materials include LSO, LYS 0, MLS, LGSO, LaBr, CsI(Ti), and mixtures thereof. It should be appreciated that other scintillator materials can be used. The sensor tiles 36 are selected to have high gain and stability and to be low cost and low operating voltage. Suitable sensor tiles include both analog or digital silicon photomultipliers (SiPMs).

Referring again to FIG. 1, a scan controller 40 controls a gradient controller 42 which causes the gradient coils 16 to apply selected magnetic field gradient pulses across the imaging region, as may be appropriate to a selected magnetic resonance imaging or spectroscopy sequence. The scan controller 40 also controls an RF transmitter 44 which causes the TEM resonator elements 18 to generate magnetic resonance excitation and manipulation $B_1$ pulses. The scan controller also controls an RF receiver 46 which is connected to the TEM resonator elements 18 to receive magnetic resonance signals therefrom. The received data from the receiver 46 is temporarily stored in a data buffer 48 and processed by a magnetic resonance data processor 50. The magnetic resonance data processor can perform various functions as are known in the art, including MR image reconstruction, magnetic resonance spectroscopy, and the like.

The scanner controller 40 also controls the PET detector modules 24 for radiation detection 40. A radiation detection circuit 52 and time stamp compliment 54 perform detection and time stamping functions not performed by the ASICs 38. A coincidence detector 56 determines coincident pairs and the LOR defined by each coincident pair. Optionally, a TOF or DOI processor 58 extracts time of flight or depth of interaction information. A reconstruction processor 60 reconstructs the LORs into a PET image representation.

Reconstructed magnetic resonance images, spectroscopy readouts, and other processed MR data combined in any of a variety of selectable ways by fusion processor 62 and MR, PET, and combined or fused images are displayed on a graphic user interface 64. The graphic user interface 64 also includes a user input device which a clinician can use for controlling the scan controller 40 to select scanning sequences and protocols, fused image combinations, and the like.

Figure 3:
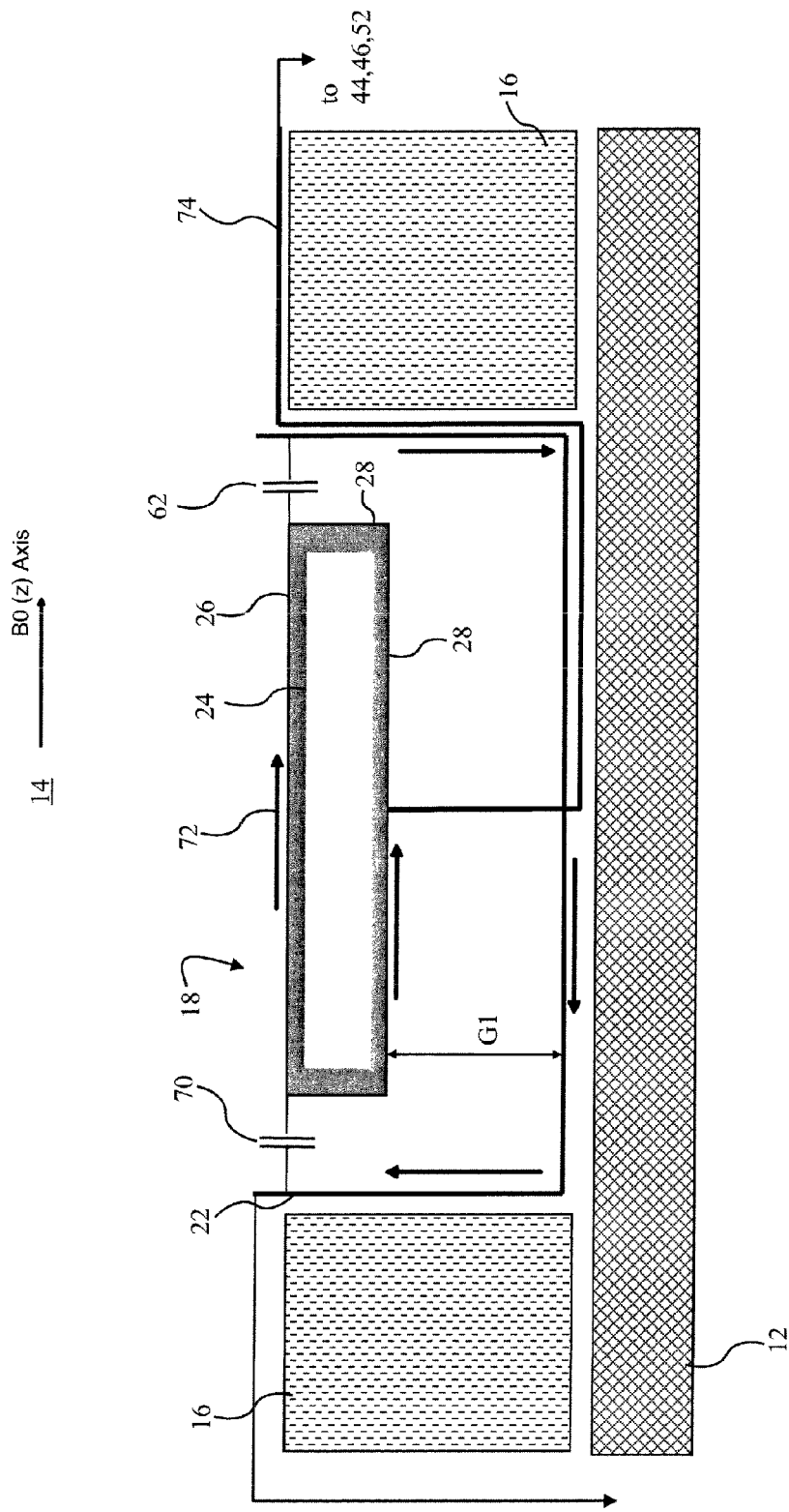
FIG. 3 is a schematic view of a resonator element and nuclear detector module spaced from an RF screen improve sensitivity.

With reference to FIG. 3, a magnified cross section of a TEM element 18 is shown in detail situated in between the gradient coils 16 and adjacent the main magnet 12 and the examination region 14. Resonating capacitors 70, which couple each element 18 to the RF screen 22, are tuned to the resonant frequency of the TEM element and collectively the TEM coil. To improve SNR, spacing between each TEM element and the RF screen is maximized to improve sensitivity by forcing the current to flow on a path 72 along the faces of the of the TEM element, particularly the face 26, adjacent to the examination region 14. The other faces 28 of the TEM element are designed to have high ohmic resistances to force currents to the face 26. This arrangement creates a field free region between the TEM elements 18 and the RF screen 22 and allows feed lines 74 to transport RF communication signals to and from the resonator elements, the PET signals from the PET detectors, and cooling to the PET detectors without interference or coupling from the RF and gradient fields.

Figure 4:
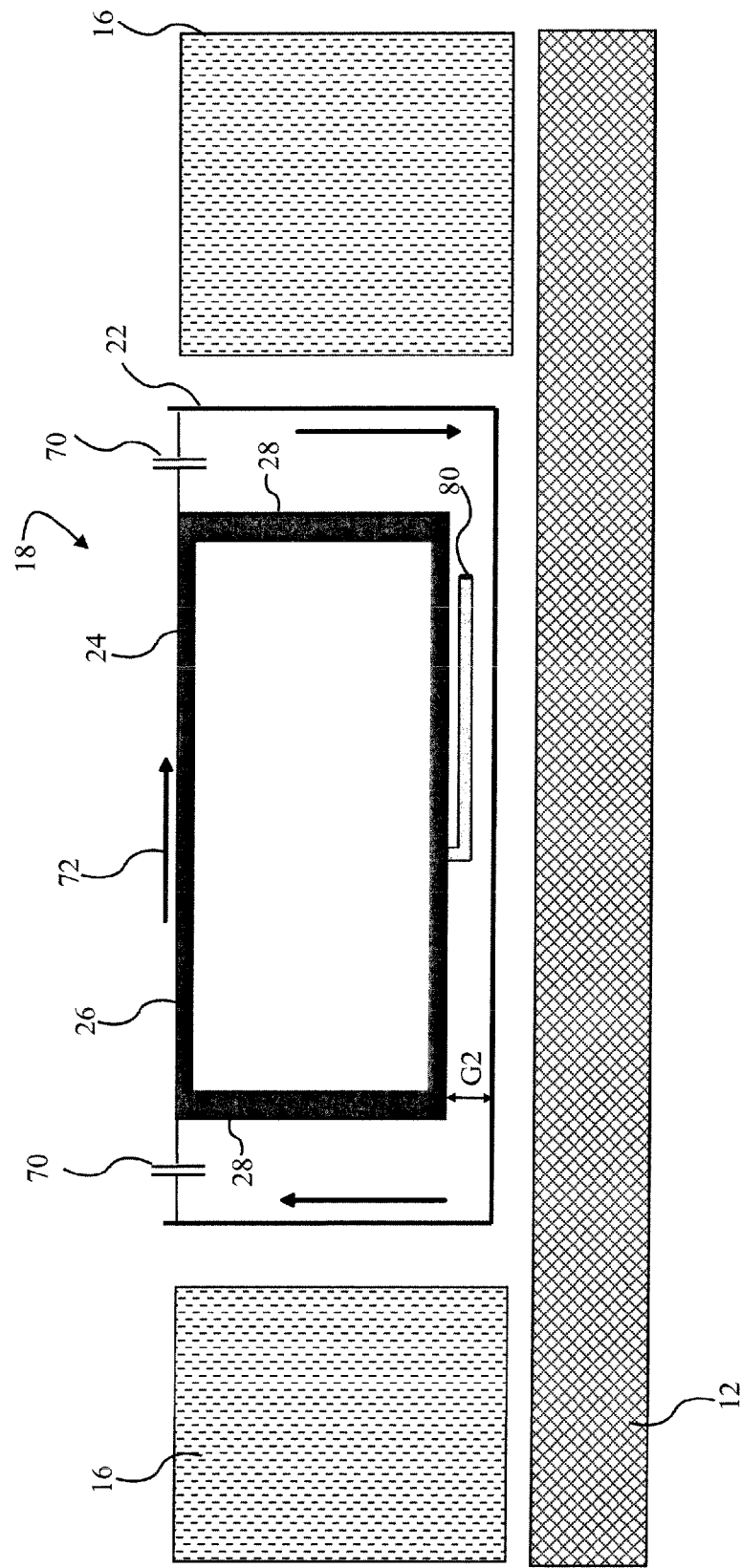
FIG. 4 is a schematic view of a resonator element and a radiofrequency trap that permits closer spacing to an RF screen and allows for a larger resonator element and housed nuclear detector module.

With reference to FIG. 4, an alternative configuration includes a larger effective resonator element box volume which can accommodate additional PET detector modules or PET specific circuitry. As noted above, sensitivity and SNR are directly related to the spacing between the resonator elements 18 and the RF screen 22. Rather than a larger gap G1 of the embodiment of FIG. 3, a smaller gap G2 can still maintain or improve the sensitivity by adding at least one quarter-wavelength resonator 80, e.g. a bazooka balun, to the resonator element. The quarter-wavelength resonator traps unwanted currents on the bottom or sides of the resonator box. As a result, resonator box currents are forced to the surface 26 adjacent to the examination region.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A combined MR and nuclear imaging unit comprising of:
   an electrically conductive hollow resonator element;
   a nuclear detector module mounted within the resonator element; and
   an RF screen adjacent to the resonator element;
   wherein each resonator element is electronically coupled to the RF screen by capacitors configured to tune an operating frequency of the resonator element to an MRI frequency.

2. A combined MR and nuclear imaging system comprising:
   a main magnet;
   a gradient coil which defines an annular recess therein; and
   a plurality of the combined MR and nuclear imaging units according to claim 1 disposed in the annular recess between the gradient coils.

3. The combined MR and nuclear imaging system according to claim 2, wherein:
   each of the resonator elements has an inner face which is radiation translucent facing an examination region; and a plurality of other faces disposed facing and spaced from the RF screen.

4. The combined MR and nuclear imaging system according to claim 3, wherein:
faces of the resonator element are configured to shield the nuclear detector module from RF interference.

5. The combined MR and nuclear imaging system according to claim 4, the nuclear detector module includes:
an array of scintillator crystals;
a plurality of silicon photomultiplier sensor tiles optically coupled to the array of scintillator crystals;
a plurality of ASICs electronically coupled to silicon photomultiplier sensor tiles.

6. The combined MR and nuclear imaging system according to claim 3, wherein the resonator element is configured such that current flows primarily of the inner face.

7. The combined MR and nuclear imaging system according to claim 3, a radiofrequency trap electronically connected to one of the other faces.

8. The combined MR and nuclear imaging system according to claim 2, wherein
the resonator element is electronically connected to at least one of a radiofrequency transmitter and a radiofrequency receiver;
the nuclear detector module is a PET detector module which includes timestamp circuitry and a coincidence detection unit.

9. The combined MR and nuclear imaging system according to claim 8, further including:
an MR resonance processor which processes data from the resonator elements to produce magnetic resonance image representations; and
a PET reconstruction processor which processes data from the PET detector module to produce PET imaging representations.

10. The combined MR and nuclear imaging system according to claim 9, further including:
a fusion processor which combines the MR and PET image representations; and
a user interface including a display which displays the MR, PET, or combined MR/PET image representations.

11. A method of making a combined MR and nuclear imaging unit comprising:
manufacturing a nuclear detector module;
disposing a hollow resonator element around the nuclear detector module, the resonator element having faces which shield the nuclear detector module from RF radiation,
one of the faces being translucent to γ radiation; and
wherein each resonator element is electronically coupled to an RF screen by capacitors configured to tune an operating frequency of the resonator element to an MRI frequency.

12. The method according to claim 11, further including:
mounting an RF shield in an annular recess defined in a gradient coil of a magnetic resonance system; and
mounting a plurality of the combined MR and Nuclear imaging units in the annular recess spaced from the RF screen.

13. The method according to claim 12, further included:
connecting an RF trap with one of the faces to cause RF current to flow preferentially on the radio translucent face.

14. The method according to claim 12, further including:
concurrently receiving γ radiation through the radio translucent face with the nuclear detector unit and at least one of the transmitting MR excitation signals to and receiving resonance signals from the resonator elements; and
reconstructing nuclear imaging representations from the received γ radiation and MR image representations from the received resonances signals.

15. A method of combined MR and nuclear imaging comprising:
concurrently (a) receiving γ radiation through a γ radiation translucent face of a resonator element with a nuclear detector unit which is disposed inside the resonator element and (b) at least one of transmitting MR excitation signals and receiving resonance signals with the resonator element; and
reconstructing nuclear image representations from the received γ radiation and MR image representations from the received resonance signals;
wherein the resonator element is electronically coupled to an RF screen by capacitors configured to tune an operating frequency of the resonator element to an MRI frequency.

16. The method according to claim 15, further including:
configuring the resonator element such that current flows primarily on the radiation translucent face.

17. The method according to claim 16, further including:
electronically connecting a radiofrequency trap to at least one of other faces of the resonator element.

18. The method according to claim 15, wherein the nuclear detector module is a PET detector module.

* * * * *